(12) United States Patent
Gu et al.

(10) Patent No.: US 12,736,524 B2
(45) Date of Patent: Sep. 15, 2026

(54) RECEPTORS FOR CYCLIC DINUCLEOTIDES AND METHODS FOR SCREENING AGONISTS OR INHIBITORS THEREOF

(71) Applicant: GUANGZHOU WINKEY TECHNOLOGY CO., LTD., Guangzhou (CN)

(72) Inventors: Sujie Gu, Guangzhou (CN); Xiaobo Li, Guangzhou (CN)

(73) Assignee: GUANGZHOU WINKEY TECHNOLOGY CO., LTD., Guangzhou (CN)

( * ) Notice: Subject to any disclaimer, the term of this patent is extended or adjusted under 35 U.S.C. 154(b) by 531 days.

(21) Appl. No.: 18/374,035

(22) Filed: Sep. 28, 2023

(65) Prior Publication Data

US 2024/0019418 A1 Jan. 18, 2024

Related U.S. Application Data

(63) Continuation-in-part of application No. 16/833,639, filed on Mar. 29, 2020, now abandoned, which is a continuation of application No. PCT/CN2018/103431, filed on Aug. 31, 2018.

(30) Foreign Application Priority Data

Oct. 11, 2017 (CN) ......................... 201710949587.4

(51) Int. Cl.
*G01N 33/50* (2006.01)
*C07K 14/705* (2006.01)
*C12N 5/07* (2010.01)
*C12N 15/63* (2006.01)

(52) U.S. Cl.
CPC ....... *G01N 33/5023* (2013.01); *C07K 14/705* (2013.01); *C12N 5/06* (2013.01); *C12N 15/63* (2013.01); *C12N 2503/02* (2013.01)

(58) Field of Classification Search
None
See application file for complete search history.

(56) References Cited

FOREIGN PATENT DOCUMENTS

WO WO-2018200812 A1 * 11/2018 .............. A61P 33/00

OTHER PUBLICATIONS

Bowei Liu et al., A cell-based high throughput screening assay for the discovery of cGAS-STING pathway agonists, Antiviral Res., Oct. 2, 2017, pp. 37-46, No. 147.

* cited by examiner

*Primary Examiner* — Aaron A Priest

(57) ABSTRACT

Disclosed herein is a recombinant vector being capable of expressing a novel receptor that senses exogenous cyclic dinucleotides (subtype M of STING) and meanwhile disclosed herein are a method and a kit for specifically identifying and detecting the expression of the said receptor. Further, provided herein are a medicament screening model and a kit for screening agonists or inhibitors targeting subtype M of the novel gene STING and the use thereof. Use of the screening model and the kit could simplify the screening procedure, enhance the screening efficiency and expand the range of the medicaments to be screened.

6 Claims, 4 Drawing Sheets

Specification includes a Sequence Listing.

SEQUENCE LISTING

```
Sequence total quantity: 9
SEQ ID NO: 1            moltype = DNA  length = 2179
FEATURE                 Location/Qualifiers
source                  1..2179
                        mol_type = genomic DNA
                        organism = Mus sp.
SEQUENCE: 1
tgaaactatt aaattccttg ctcagatttc aggaagtaaa gtgtgctgtt catctcaatc  60
tctcctgtct aacccctccc ctcccgattt ccgggggatc aatgatagta gagagctttg  120
gggcctctgg aaatcctgtg gggccctgtc acttttggtc cttgtatgga gtcctgctag  180
gtgtccactg gagtgtgtta catctcggga cctttagagg aattcggagt gcggggctgt  240
ggctgctgtc tccccattca gaagccactt gctagtagct actgaaaggc tcttcattgt  300
ctcttctgct ccaggaacac cggtctagga agcagaagat gccatactcc aacctgcatc  360
cagccatccc acggcccaga ggtcaccgct ccaaatatgt agccctcatc tttctggtgg  420
ccagcctgat gatcctttgg gtggcaaagg atccaccaaa tcacactctg aagtacctag  480
cacttcacct agcctcgcac gaacttggac tactgttgaa aaacctctgc tgtctggctg  540
aagagctgtg ccatgtccag tccagttgga tgtttggcct tctggtcctc tataagtccc  600
taagcatgct cctgggcctt cagagcttga ctccagcgga agtctctgca gtctgtgaag  660
aaaagaagtt aaatgttgcc cacgggctgg cctggtcata ctacattggg tacttgcggt  720
tgatcttacc agggctccag gcccggatcc gaatgttcaa tcagctacat aacaacatgc  780
tcagtggtgc agggagccga agactgtaca tcctctttcc attggactgt ggggtgcctg  840
acaacctgag tgtagttgac cccaacattc gattccgaga tatgctgccc cagcaaaaca  900
tcgaccgtgc tggcatcaag aatcgggttt attccaacag cgtctacgag attctggaga  960
acggacagcc agcaggcgtc tgtatcctgg agtacgccac cccttgcag acccctgtttg  1020
ccatgtcaca ggatgccaaa gctggcttca gtcgggagga tcggcttgag caggctaaac  1080
tcttctgccg gacacttgag gaaatcctgg aagatgtccc cgagtctcga aataactgcc  1140
gcctcattgt ctaccaagaa cccacagacg gaaacagttt ctcactgtct caggaggtgc  1200
tccggcacat tcgtcaggaa gaaaaggagg aggttaccat gaatgccccc atgacctcag  1260
tggcacctcc tccctccgta ctgtcccaag agccaagact cctcatcagt ggtatggatc  1320
agcctctccc actccgcact gacctcatct gaggcatggg acagccttgt ctgggctcta  1380
gtgatccttt agcctcctga ctgagccttc cttcaatggt tgggggcctc agagacttca  1440
catctccaga tgagtcccac attcctgggc aagccattta tttcacctct ctgagcctca  1500
accaacccta ctatgaaagg aggtcataat gcgttccctg cccagccaaa ggattttata  1560
tatgtagaag ttggtgtcaa tgcctggtaa acttgagaga aaggccaagt acttcccgtg  1620
gatgctgcag acattccctg ctctctgttg acctgtgtgg atggtaccag cagacttcca  1680
accctccagc ttctggtcac gtgtgttcaa tgggagctta agtagatggc gagagggaga  1740
aggaacattt gttctgttag ctgtatacaa tcacagtggg ctggcctgtc aactgccttc  1800
ttaataaaca tatctattct cagatttcta gaatggcctc ttccccttgt ctctagcact  1860
ggtatttgtg tgacactgga gtactttctg tctggtctct ttatatcatg tcccttgcac  1920
atggtgttgg catcaggacg tcccaaactc atgacatcac ataggcgaca gcatgacctg  1980
caacctgcag accggttgcc aagacaacag gcaccatatt cccaccttcc acttggctca  2040
cctcccacct ttacctgtgt tacgtcatct tccatatctt ccatacgtct tccatcttcc  2100
atacgtctct ctcccctgct tctctttctg ctgctacctt gtctctccct tccaataaaa  2160
cctcttccat gcggaactg                                                2179
```

```
SEQ ID NO: 2            moltype = DNA  length = 1907
FEATURE                 Location/Qualifiers
source                  1..1907
                        mol_type = genomic DNA
                        organism = Homo sapiens
SEQUENCE: 2
agaaaaagaa tctgcatcct ggaaaccaga agaaaaatat gagacgggga atcatcgtgt  60
gatgtgtgtg ctgcctttgg ctgagtgtgt ggagtcctgc tcaggtgtta ggtacagtgt  120
gtttgatcgt ggtggcttga ggggaacccg ctgttcagag ctgtgactgc ggctgcactc  180
agagaagctg cccttggctg ctcgtagcgc cgggccttct ctcctcgtca tcatccagag  240
cagccagtgt ccgggaggca gaaggtaccg gggcagctac tggaggactg tgcgggcctg  300
cctgggctgc cccctccgcc gtggggccct gttgctgctg tccatctatt tctactactc  360
cctcccaaat gcggtcggcc cgcccttcac ttggatgctt gccctcctgg gcctctcgca  420
ggcactgaac atcctcctgg gcctcaaggg cctggcccca gctgagatct ctgcagtgtg  480
tgaaaaaggg aatttcaacg tggcccatgg gctggcatgg tcatattaca tcggatatct  540
gcggctgatc ctgccagagc tccaggcccg gattcgaact tacaatcagc attacaacaa  600
cctgctacgg ggtgcagtga gccagcggct gtatattctc ctcccattgg actgtggggt  660
gcctgataac ctgagtatgg ctgaccccaa cattcgcttc ctggataaac tgccccagca  720
gaccggtgac catgctggca tcaaggatcg ggtttacagc aacagcatct atgagcttct  780
ggagaacggg cagcgggcgg gcacctgtgt cctggagtac gccacccccct tgcagacttt  840
gtttgccatg tcacaataca gtcaagctgg ctttagccgg gaggataggc ttgagcaggc  900
caaactcttc tgccggacac ttgaggacat cctggcagat gcccctgagt ctcagaacaa  960
ctgccgcctc attgcctacc aggaacctgc agatgacagc agcttctcgc tgtcccagga  1020
ggttctccgg cacctgcggc aggaggaaaa ggaagaggtt actgtgggca gcttgaagac  1080
ctcagcggtg cccagtacct ccacgatgtc ccaagagcct gagctcctca tcagtggaat  1140
ggaaaagccc ctccctctcc gcacggattt ctcttgagac ccagggtcac caggccagag  1200
cctccagtgg tctccaagcc tctggactgg gggctctctt cagtggctga atgtccagca  1260
gagctatttc cttccacagg gggccttgca gggaagggtc caggacttga catcttaaga  1320
tgcgtcttgt ccccttgggc cagtcatttc ccctctctga gcctcggtgt cttcaacctg  1380
tgaaatggga tcataatcac tgccttacct ccctcacggt tgttgtgagg actgagtgtg  1440
tggaagtttt tcataaactt tggatgctag tgtacttagg gggtgtgcca ggtgtctttc  1500
atggggcctt ccagacccac tccccaccct tctccccttc ctttgcccgg ggacgccgaa  1560
ctctctcaat ggtatcaaca ggctccttcg ccctctggct cctggtcatg ttccattatt  1620
ggggagcccc agcagaagaa tggagaggag gaggaggctg agtttggggt attgaatccc  1680
ccggctccca ccctgcagca tcaaggttgc tatggactct cctgccgggc aactcttgcg  1740
taatcatgac tatctctagg attctggcac cacttccttc cctggcccct taagcctagc  1800
tgtgtatcgg caccccccacc ccactagagt actccctctc acttgcggtt tccttatact  1860
ccaccccttt ctcaacggtc ctttttaaa gcacatctca gattacc               1907

SEQ ID NO: 3            moltype = AA  length = 337
FEATURE                 Location/Qualifiers
source                  1..337
                        mol_type = protein
                        organism = Mus sp.
SEQUENCE: 3
MPYSNLHPAI PRPRGHRSKY VALIFLVASL MILWVAKDPP NHTLKYLALH LASHELGLLL  60
KNLCCLAEEL CHVQSSWMFG LLVLYKSLSM LLGLQSLTPA EVSAVCEEKK LNVAHGLAWS  120
YYIGYLRLIL PGLQARIRMF NQLHNNMLSG AGSRRLYILF PLDCGVPDNL SVVDPNIRFR  180
DMLPQQNIDR AGIKNRVYSN SVYEILENGQ PAGVCILEYA TPLQTLFAMS QDAKAGFSRE  240
DRLEQAKLFC RTLEEILEDV PESRNNCRLI VYQEPTDGNS FSLSQEVLRH IRQEEKEEVT  300
MNAPMTSVAP PPSVLSQEPR LLISGMDQPL PLRTDLI                         337

SEQ ID NO: 4            moltype = AA  length = 260
FEATURE                 Location/Qualifiers
source                  1..260
                        mol_type = protein
                        organism = Homo sapiens
SEQUENCE: 4
MLALLGLSQA LNILLGLKGL APAEISAVCE KGNFNVAHGL AWSYYIGYLR LILPELQARI  60
RTYNQHYNNL LRGAVSQRLY ILLPLDCGVP DNLSMADPNI RFLDKLPQQT GDHAGIKDRV  120
YSNSIYELLE NGQRAGTCVL EYATPLQTLF AMSQYSQAGF SREDRLEQAK LFCRTLEDIL  180
ADAPESQNNC RLIAYQEPAD DSSFSLSQEV LRHLRQEEKE EVTVGSLKTS AVPSTSTMSQ  240
EPELLISGME KPLPLRTDFS                                             260

SEQ ID NO: 5            moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 5
actgcggctg cactcaga                                               18

SEQ ID NO: 6            moltype = DNA  length = 22
FEATURE                 Location/Qualifiers
misc_feature            1..22
                        note = Synthetic
```

-continued

```
source                  1..22
                        mol_type = other DNA
                        organism = synthetic construct
SEQUENCE: 6
accatgccag cccatgggcc ac                                        22

SEQ ID NO: 7            moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 7
gctgtgccat gtccagtc                                             18

SEQ ID NO: 8            moltype = DNA  length = 23
FEATURE                 Location/Qualifiers
misc_feature            1..23
                        note = Synthetic
source                  1..23
                        mol_type = other DNA
                        organism = synthetic construct
SEQUENCE: 8
agccagtgtc cgggaggcag aag                                       23

SEQ ID NO: 9            moltype = DNA  length = 18
FEATURE                 Location/Qualifiers
misc_feature            1..18
                        note = Synthetic
source                  1..18
                        mol_type = other DNA
                        organism = synthetic construct
SEQUENCE: 9
caaccgcaag tacccaat                                             18
```

RECEPTORS FOR CYCLIC DINUCLEOTIDES AND METHODS FOR SCREENING AGONISTS OR INHIBITORS THEREOF

CROSS-REFERENCE TO RELATED APPLICATIONS

This present application is a Continuation-in-part Application of U.S. patent application Ser. No. 16/833,639 filed on Mar. 29, 2020, which is a Continuation Application of PCT application No. PCT/CN2018/103431 filed on Aug. 31, 2018, which claims the priority of Chinese Patent Application No. 201710949587.4 filed on Oct. 11, 2017. The contents of the above-identified applications are hereby incorporated by reference.

REFERENCE TO SEQUENCE LISTING

The Sequence Listing XML file submitted via the USPTO Patent Center, with a file name of "Sequence-_Listing.XML", a creation date of Sep. 27, 2023, and a size of 15 KB, is part of the specification and is incorporated in its entirety by reference herein.

FIELD OF THE DISCLOSURE

The present disclosure relates to bioengineering field and medicaments screening field, more particularly, to a receptor that senses an exogenous cyclic dinucleotide and a gene encoded by the said receptor, a vector for the said receptor, an identification method for the said receptor, an expression measurement for the said receptor and a stable cell line for the said receptor and use of the said receptor in screening medicaments as well as related kits.

BACKGROUND OF THE DISCLOSURE

Cyclic dinucleotides (including c-di-AMP and c-di-GMP deviated from bacteria and cGAMP deviated from mammalian cells) are capable of activating signal pathway STING-TBK1-IRF3, so as to stimulate organisms to produce strong immune response. Recent researches demonstrate that exogenous cyclic dinucleotides are capable of notably increasing immune response of vaccines. Meanwhile, recent researches show that the exogenous cyclic dinucleotides exhibit excellent efficiency in anti-tumor immunology treatment. The exogenous cyclic dinucleotides could activate attacking effect of CD4 and CD8 cells against tumors with specificity in vivo and in vitro, thereby inhibiting growth of tumors. Therefore, the cyclic dinucleotides can be considered as a new generation of vaccine adjuvants and medicaments for treatment of tumors. In March, 2015, Noratis and Aduro made a deal with 750 million US dollars to co-develop a novel targeted medicament against STING.

The receptor of the cyclic dinucleotides is considered as subtype 1 of protein STING, which is located on intracellular endoplasmic reticulum (ER). Such receptor is encoded by Tmem173 gene. Since extracellular cyclic dinucleotides cannot directly pass through cell membranes while the endoplasmic reticulum is within cytoplasm, it does not know how the exogenous cyclic dinucleotides activate receptor subtype 1 of protein STING on the endoplasmic reticulum by passing through the structure of cell membranes. Therefore, current theories cannot be used to explain how the exogenous cyclic dinucleotides activate immune response within organisms. When screening inhibitors and agonists for the cyclic dinucleotides, it needs to treat cells with cell membrane permeability procedure or use liposomes to encapsulate medicaments to be screened for transfection, so as to allow the medicaments to be screened to contact subtype 1 of STING on the endoplasmic reticulum. As such, screening efficiency and the medicaments that can be screened are significantly reduced (e.g., the medicaments to be screened need to be encapsulated by liposomes), and meanwhile, there are limitations for the extracellular cyclic dinucleotides used as vaccine adjuvants and for anti-tumor immunology treatment.

The present disclosure provides a recombinant vector being capable of expressing a novel receptor that senses the exogenous cyclic dinucleotides (referred as a subtype M of STING) and a method and a kit for specifically identifying and detecting the expression of such receptor. Further, the present disclosure provides a medicament screening model and a kit targeting the new gene subtype M of STING and the use thereof.

SUMMARY OF THE DISCLOSURE

In one aspect, the inventor, by analyzing whole transcriptome data, found that Tmem173 gene could encode subtypes (named by the inventor as subtype M of human STING and subtype M of mouse STING, hereinafter collectively referred to as subtype M of STING) of STING expressing on the cell surface, in addition to conventional type of STING (subtype 1 of STING) on endoplasmic reticulum. Through 5'RACE method, the inventor confirmed that subtype M of STING widely exists in human and mouse as well as tumor cell lines. In in vitro studies, it was found that these subtypes M of STING can directly sense extracellular cyclic dinucleotides, so as to be used as a receptor of extracellular cyclic dinucleotides. The extracellular cyclic dinucleotides can activate subtype M of STING, thereby activating the promotor of downstream type 1 interferon, and in turn facilitating up-regulation of the expression of type 1 interferon. Therefore, subtype M of STING, as the receptor of exogenous cyclic dinucleotides, is a critical target for development of vaccines and tumor immunology treatment.

The inventor found that subtype M of STING encoded by Tmem173 gene is located on the cell membranes and in the endoplasmic reticulum. The amino acid sequence of subtype M of mouse STING is set forth in SEQ ID NO:3. The amino acid sequence of subtype M of human STING is set forth in SEQ ID NO:4.

In another aspect, the present disclosure provides a recombinant vector for expressing subtype M of STING. For example, it may be Pcmv6-Entry containing DNA sequence as mentioned above.

In another aspect, the present disclosure provides a method for screening agonists or inhibitors for receptors of extracellular cyclic dinucleotides, containing the following steps: culturing cells containing a nucleotide sequence set forth in SEQ ID NO: 1 or SEQ ID NO: 2; adding medicaments to be screened to a culture medium in which the cells are cultured, incubating the cells, detecting the content of type 1 interferon or NF KappaB within the cells or cell culture medium, or dynamically monitoring the reporter fluorescein produced by the cells to which the medicaments are added by a photometer; and screening out the medicaments for increasing or inhibiting the expression of type 1 interferon or a reporter gene.

The existing subtype 1 of STING is located in the cytoplasm and the ligand it recognizes can only be intracellular cyclic dinucleotides. The inventors unexpectedly discover that the subtype M gene of human STING or subtype M gene of mouse STING can be expressed on cell membranes. As a result, the subtype M protein of STING (whose amino acid sequence is shown in SEQ ID NO: 3 or SEQ ID NO: 4) located on the cell membrane can directly sense extracellular cyclic dinucleotides and act as a receptor for extracellular cyclic dinucleotides.

Based on the characteristics above, the method of the present application, compared to the prior art, omits the need to add additional reagents to the cell culture medium for perforation of cell membranes (e.g., utilizing perfringolysin-O (PFO) or digitonin), or omits the step of encapsulating medicaments with liposomes to help candidate molecules pass through the cell membranes and enter the cytoplasm to activate subtype 1 of STING. Therefore, the method of the present application significantly simplifies the screening procedure of medicaments and expands the range of medicaments that can be screened (for example, the medicaments do not need to have the characteristic that can be encapsulated by liposomes).

In some embodiments, the receptor of extracellular cyclic dinucleotides is a subtype M protein of human STING (whose amino acid sequence is shown in SEQ ID NO: 4) or a subtype M protein of mouse STING (whose amino acid sequence is shown in SEQ ID NO: 3).

In some embodiments, the reporter gene is the gene of fluorescein.

In some embodiments, the cells are selected from the group consisting of HEK293T cells, mouse spleen lymphocytes, Hela cells, peripheral blood mononuclear cells (PBMC), CD4 cells, and CD8 cells.

In some embodiments, the medicaments to be screened are selected from the group consisting of synthetic chemical compounds, natural compounds, biological medicaments and Chinese medicine monomer.

The present disclosure also provides a cell line, containing a subtype M gene of human STING or a subtype M gene of mouse STING, wherein a nucleotide sequence of the subtype M gene of human STING is set forth in SEQ ID NO:2, or is a nucleotide sequence encoding the amino acid sequence set forth in SEQ ID NO:4, and a nucleotide sequence of the subtype M gene of mouse STING is set forth in SEQ ID NO:1, or is a nucleotide sequence encoding the amino acid sequence set forth in SEQ ID NO:3.

Further, the cell line includes a reporter gene for indicating that the subtype M gene of human STING or the subtype M gene of mouse STING is activated. Preferably, the reporter gene is located downstream of type 1 interferon or NK KappaB reaction element promoter.

Further, the cell line includes a recombinant expression vector whose sequence is the nucleotide sequence set forth in SEQ ID NO:1 or SEQ ID NO:2, or a recombinant expression vector whose sequence is the nucleotide sequence encoding the amino acid sequence set forth in SEQ ID NO:3 or SEQ ID NO:4.

Further, the cells are animal cells that do not themselves express the subtype M gene of STING. Optionally, the cells are human cells, wherein the subtype M gene of human STING is replaced with the subtype M gene of mouse STING; or the cells are mouse cells, wherein the subtype M gene of mouse STING is replaced with the subtype M gene of human STING.

In still another aspect, the present disclosure provides a method and a kit for specifically identifying and detecting the mRNA level of subtype 1 and subtype M of STING. The basic principle of the kit for detection comprises utilization of oligonucleotide primers with specificity, amplification of targeting nucleotides by RT-PCR amplification in RT-PCR reaction buffer solution containing reverse transcriptases, Taq DNA polymases, RNase inhibitors, deoxyribonucleoside triphosphates (dNTPs) with high quality and Mg2+ and the like, so as to quantitatively detect the mRNA level of subtype 1 and subtype M of STING with increased speed, high efficiency, and great specificity.

The kit as provided herein comprises a plurality of vials or tubes with caps for seal, each of which comprises RNA extracting reagents, RT-PCR amplification reacting solution, mixed enzymes, negative quality controls, positive quality controls, mRNA positive standards for subtype 1 and subtype M of STING, and packing boxes for separating and collecting the said vials or tubes. The mixed enzymes comprise Taq DNA polymases and reverse transcriptases (RT enzymes). The RT-PCR amplification reacting solution comprises the following oligonucleotide primers or the sequences with more than 85% homology with the following sequences or one or combination of the following sequences.

| Primiers | Forward (5'→3') | Primers | Backward (5'→3') |
|---|---|---|---|
| hIsoform M-F-1 | **ACTGCGGCTGCACTCAGA** (SEQ ID NO.: 5) | hIsoforms M-F-2 | **AGCCAGTGTCCGGGAGGCAGAAG** (SEQ ID NO.: 8) |
| hIsoforms M-commonR | **ACCATGCCAGCCCATGGGCCAC** (SEQ ID NO.: 6) | | |
| mIsoform M-F | **GCTGTGCCATGTCCAGTC** (SEQ ID NO.: 7) | mIsoform M-R | **CAACCGCAAGTACCCAAT** (SEQ ID NO.: 9) |

The RT-PCR amplification reacting solution further comprises DNTPs, PCR Buffer and RNase inhibitors. The products obtained from RT-PCR amplification can be semi-quantified by electrophoresis (see FIGS. 1A and 1B) or can be accurately quantified by targeted sequencing using Ion Torrent.

The present disclosure further provides a method and a kit for specifically identifying and detecting the protein contents of subtype 1 and subtype M of STING. The basic principle of the kit for detection as provided herein is Western-blot technology, for quantitatively detecting protein expression level of subtype 1 and subtype M of STING with increased speed, high efficiency and great specificity.

The kit as provided herein comprises solutions for treating samples, pre-made gels for Western-blot, PVDF membranes for transmembrane, anti-subtype 1 and anti-subtype M of STING antibodies, secondary antibodies, protein positive standards for subtype 1 and subtype M of STING, and reagents for color development. Preferably, the samples are treated by the solutions for treating samples in the kit and the Western-blot experiments are carried out. The protein expression levels of subtype 1 and subtype M of STING can be semi-quantified by the stripes of targeting proteins (see FIGS. 2A and 2B) and comparing standards of subtype 1 and subtype M of STING.

In yet another aspect, the present disclosure provides a vector for preparing lentivirus of subtype 1 and subtype M of STING. Preferably, the vector can be used to stably express subtype 1 and subtype M of STING in vivo or in vitro.

In addition, the present disclosure further provides a cell line for stably expressing subtype M of STING. Preferably, the cell lines further comprise reporter genes, for indicating that the subtype M of STING is activated or inhibited. More preferably, the reporter genes are located downstream of type 1 interferon or NF kappB reaction element promoter. The present disclosure further provides a method and a kit for screening agonists and/or inhibitors for subtype M of STING by using the said cell lines.

The kit as provided herein comprises cell lines for stably expressing subtype M of STING. Preferably, the cell lines further comprise reporter genes, for indicating that the subtype M of STING is activated or inhibited. More preferably, the reporter genes are located downstream of type 1 interferon or NF kappB reaction element promoter. Preferably, the kit may further comprise a substrate on which the reporter genes act, and cell lysates. Preferably, the agonists and inhibitors for subtype M of STING can be effectively screened out by the method as shown in FIG. 4 using the kit as provided herein.

It can be seen that, the subtype M of STING is firstly found as a receptor that senses extracellular cyclic dinucleotides, which can be stably expressed in eukaryocytes. The extracellular cyclic dinucleotides exhibit great efficiency in tumor immunology treatment and development of vaccines, which indicates that the receptors for the extracellular cyclic dinucleotides, i.e., the subtype M of STING as described herein, is a critical target for tumor immunology treatment. Development and optimization of medicaments screening based on the receptor for the extracellular cyclic dinucleotides (subtype M of STING) play a key role in development of vaccines and tumor immunology treatment. Moreover, the expression level of the said receptor will be a key marker for drug sensitivity for treatment using the extracellular cyclic dinucleotides and other agonists for STING. The specific identification and the method and the kit for detection of mRNA level and protein level of subtype M of STING as described herein will play a critical role in detecting such marker. Development of vaccines and tumor immunology treatment based on the subtype M of STING can be facilitated by high-throughput screening for small molecule medicaments and screening for antibody medicaments according to the present disclosure.

So far, there are only several naturally-existing cyclic dinucleotides as agonists for STING, while no inhibitor for STING is found. The present disclosure provides a new platform for effectively, reliably and easily screening agonists and inhibitors for STING, which is suitable for high-throughput medicament screening and has significance for finding out agonists and inhibitors of the receptors for the cyclic dinucleotides.

DETAILED DESCRIPTION OF THE DISCLOSURE

Figure 1A:
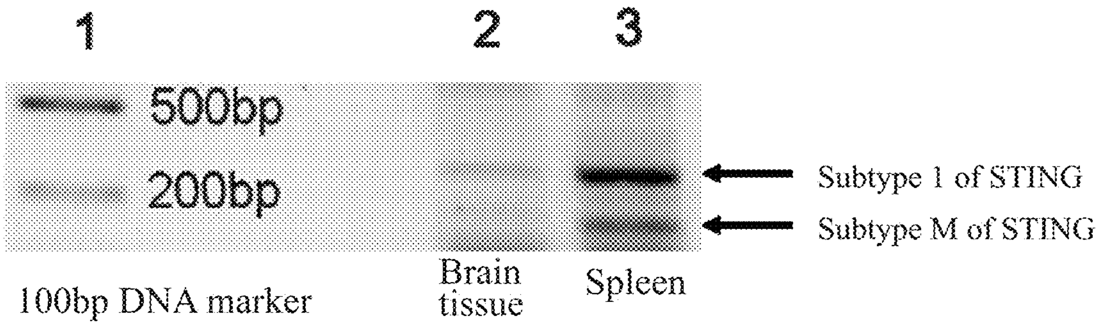
FIGS. 1A and 1B show RT-PCR electrophoresis results for specific fragments of subtype M of STING from mouse brain tissues and splenic lymphocytes as well as human Hela cells and peripheral blood mononuclear cells (PBMCs), in which, Lane 1 is 100 bp Marker, Lanes 2 and 3 in FIG. 1A are the RT-PCR electrophoresis results for subtype 1 and subtype M of mouse STING from mouse brain tissues and splenic lymphocytes. Sanger sequencing results demonstrate that the stripes as shown are subtype 1 and subtype M of STING respectively. Lanes 2 and 3 in FIG. 1B are the RT-PCR electrophoresis results for subtype 1 and subtype M of human STING from human Hela cells and PBMCs. Sanger sequencing results demonstrate that the stripes as shown are subtype 1 and subtype M of STING respectively.

Several aspects of the disclosure are described below in details by reference to appended drawings and specific embodiments. The skilled in the art should understand that the embodiments are set forth to provide an illustration, rather than limit the scope of the present disclosure. The scope of the present disclosure is limited by the appended claims.

The terminology used herein is for the purpose of describing particular embodiments only and is not intended to be limiting of the disclosure. As used herein, the singular forms "a", "an" and "the" are intended to include the plural forms as well, unless the context clearly indicates otherwise.

Example 1: Construction and Identification of Gene Expression Plasmid of Subtype M of Human and Subtype M of Mouse STING and Identification of Gene Expression Level of Subtype M of Human and Mouse STING Based on high-throughput RNA sequencing, we found that Tmem173 could encode other subtypes of STING (named as subtype M of STING), in addition to subtype 1 of STING.

In order to confirm existence of subtype M of human and subtype M of mouse STINGs, we designed specific primers to specifically amplify subtypes M of human and mouse STINGs. In brief, total RNA was prepared by using RNA extraction reagents from wild-type mouse splenic cells or human PBMCs. Then the RNA was reversely transcribed to cDNA by using a reverse transcription kit (Invitrogen, 18080-051) according to the manufacturer's instructions. The primers for amplifying subtype M gene of human and subtype M of mouse STINGs were listed as below.

| Primer | Forward (5'→3') | Primer | Backward (5'→3') |
|---|---|---|---|
| hIsoform M-F-1 | **ACTGCGGCTGCACTCAGA** (SEQ ID NO.: 5) | hIsoforms M-F-2 | **AGCCAGTGTCCGGGAGGCAGAAG** (SEQ ID NO.: 8) |
| hIsoforms M-commonR | **ACCATGCCAGCCCATGGGCCAC** (SEQ ID NO.: 6) | | |
| mIsoform M-F | **GCTGTGCCATGTCCAGTC** (SEQ ID NO.: 7) | mIsoform M-R | **CAACCGCAAGTACCCAAT** (SEQ ID NO.: 9) |

For subtype M of mouse STING, only primer mIsoform M-F/R was used for performing one-round PCR amplification in mouse splenic cells. For subtype M of human STING, nested PCR was carried out to amplify specific sequences. Human PBMCs cDNA was used as a first-round PCR template with outer primers (hIsoform M-F-1 and hIsoforms M-commonR). The products from the first-round PCR was used as the templates for carrying out the second-round PCR (using primers hIsoforms M-F-2 and hIsoforms M-commonR). The resultant sequences specific for subtype M of human and subtype M of mouse STINGs were consistent with subtypes M of human and mouse STINGs obtained by whole transcriptome sequencing. Therefore, we confirmed that subtypes M of human and mouse STINGs exist in human and mouse primary immune cells.

In order to construct recombinant expression vectors for subtypes M of human and mouse STINGs, based on the difference between subtype 1 of STING and subtype M of STING, we constructed subtype M of human STING and subtype M of mouse STING from subtype 1 of STING by performing site-directed mutagenesis in pCMV6 expression vector for expressing subtype 1 of STING. Q5 site-directed mutagenesis kit (New England Biolabs, product E0554S) was used for performing site-directed mutagenesis according to the manufacturer's instructions. The primers with specific mutation sites were designed for each mutated vector. PCR procedure for performing mutagenesis included: 94° C. for 5 min, following 37 cycles: 94° C. for 1 min, 55° C. for 30 s and 72° C. for 3 min, finally 72° C. extended for 2 min. PCR products were subject to agarose gel electrophoresis. The targeting stripes were recovered by QuickClean II gel recovery kit (Jinsirui Ltd., Product L00418) and connected by kinase-Ligase-DPNI (KLD) enzyme mixture for 10 min, and then were converted to DH5a competent cells. After 16 hours, bacterial monoclones were amplified and then the expression plasmids were purified and sequenced to confirm the accuracy of targeting sequences.

In order to construct lentivirus expression vectors for subtypes M of human and mouse STINGs, PCR amplification (94° C. for 5 min, following 40 cycles: 94° C. for 1 min, 55° C. for 1 min and 72° C. for 3 min, finally 72° C. extended for 10 min) was performed on the expression vectors for expressing subtype M of human STING and subtype M of mouse STING as mentioned above by using forward primers containing Sgf I restriction enzyme cleavage sites and backward primers containing MluI restriction enzyme cleavage sites. The targeting stripes were recovered by using QuickClean II gel recovery kit (Genscript Ltd., Product L00418) and the targeting fragments were inserted into pLenti vectors (Origene, Product RC208418L2V) with SgfI/MluI enzyme cleavage sites by using T4 DNA ligase. Then the lentivirus vectors were purified and sequenced.

Example 2: Construction of Stably Transfected Cell Lines (Take HEK293T Cell as an Example)

The lentivirus expression vector containing subtype M of human STING and subtype M of mouse STING as mentioned above was packed with Lenti-vpak packaging box (Origene, Product TR30022) so as to produce lentivirus particles.

HEK293T cells were incubated in Dulbecco's Modified Eagle Medium (DMEM) comprising 10% (v/v) fetal bovine serum and 10 units/ml penicillin-streptomycin solution at 37° C. The supernatants with lentivirus particles were added to the HEK293T culture solution to perform centrifugation infection. After transfection for 48 hours, the centrifuged HEK293T cells were re-suspended in complete growth medium containing 300 μg/ml G418. After two weeks, drug resistance strains occurred. GFP+ cells were sorted in FACSAria II cell sorter (BD biology scientific). The monoclonal cells were selected out by using limiting dilution method from the resultant GFP+ cells.

After obtaining cell lines for stably expressing subtype M of human and subtype M of mouse STINGs, HEK293T cell lines for stably expressing recombinant proteins were inoculated in 24-well culture plate ($0.2\times10^6$ cells/well) overnight. Then, the reporter genes of type 1 interferon were transiently transfected. Specifically, 3 g reporter gene plasmids with promoter genes of type 1 interferon were diluted in 150 μl serum-free DMEM medium and mixed with 150 μl serum-free DMEM medium containing 9 μl TurboFectin Transfection Reagent (OriGene Ltd., USA). Incubate for 20 min at room temperature. The supernatants of the stable cell lines were removed and the stable cell lines were added into the combined DNA-liposome complex at 300 μl/well. The 24-well plate was placed in carbon dioxide incubator and incubated at 37° C. The medium was replaced at 6 hours after transfection. The serum-free medium was replaced with complete growth medium. After 24 hours, the supernatants were removed. One group is added into complete medium containing c-di-AMP (final concentration: 30 M, (InvivoGen, Product vac-cda)). Another group is merely added into complete medium. At 16 hour after stimulating the ligands, the activity of luciferase was determined by using the substrate of the luciferase. It was found that the group with c-di-AMP had significantly increased luciferase activity compared with control group in which only transfection was performed, which indicated that subtype M of human and subtype M of mouse STINGs could be successfully expressed and play their roles.

Figure 1B:
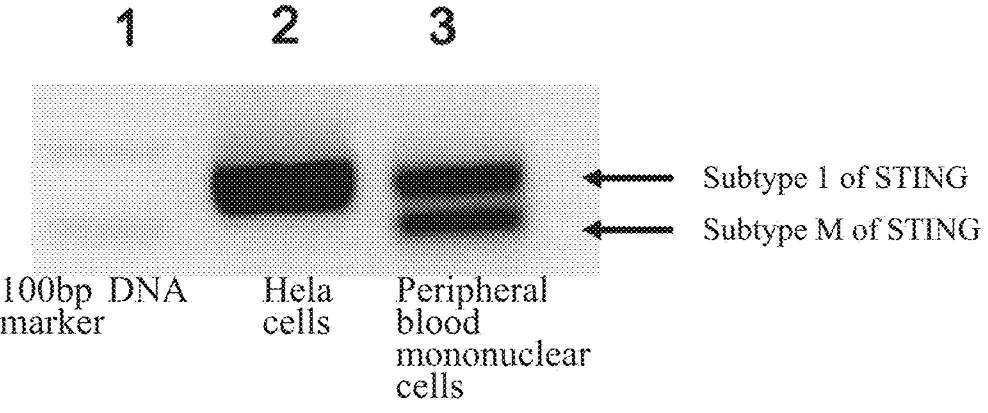

Example 3: Method and Kit for Specifically Identifying and Detecting Subtypes M of Human and Mouse STINGs The method for detecting and identifying subtypes M of human and mouse STINGs at mRNA level comprises: extracting targeting tissues or fine RNAs with the kit as mentioned above, reversely transcribing RNA to cDNA by using RT enzyme in the kit. For the subtype M of mouse STING, one-round PCR amplification was performed merely by using primer mIsoform M-F/R. For subtype M of human STING, nested PCR was performed to amplify specific sequences. Human cDNA was used as the first-round PCR template with outer primer (hIsoform M-F-1 and hIsoforms M-commonR). The products from the first-round PCR were used as a template for performing the second-round PCR (using primer hIsoforms M-F-2 and hIsoforms M-commonR). From the agarose gel electrophoresis, the stripes of subtype 1 and subtype M of mouse STING (identified by sequencing) could be seen (FIGS. 1A and 1B). Relative quantitation can be performed by comparison of the brightness of the stripes with the brightness of the housekeeping genes. The same primers could be used for next-generation sequencing, such as Ion Torrent or Illumina platform sequencing. Accurate quantitation can be performed according to the volume of reads.

Figure 2A:
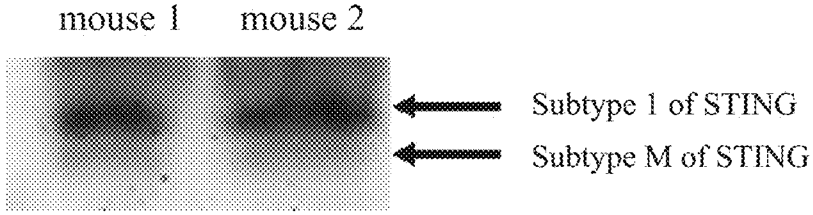
FIGS. 2A and 2B show the results of Western-blot using anti-STING antibodies on mouse splenic lymphocytes of two mice and human PBMC. The stripes as shown are subtype 1 and subtype M of STING respectively.
Figure 2B:
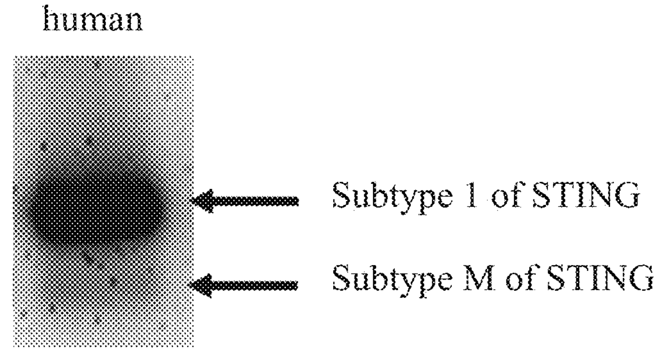

Subtype M of human and subtype M of mouse STINGs were detected and identified by conventional Western-blot method at protein level. Briefly, for preparation of targeting tissues or cells, the protein extracting solution from the kit was used to prepare protein extract (high-speed homogenizer, mortar and grinding homogenizer and ultrasonic crushing method were used). After boiling for 5 min, SDS-PAGE was performed and the proteins were transferred to nitrocellulose membranes (Bio-Rad, Product 162-0115) by using semidry process. The nitrocellulose membranes were blocked by 1×TBST containing 5% (w/v) BSA at room temperature for 2 hours. Then the nitrocellulose membranes were transferred to 1×TBST containing primary antibody (Cell Signaling, Product 13647, 1:1000 dilution) and 5% (w/v) BSA and wiggly incubated at 4° C. overnight, followed by washing with 1×TBST containing 5% (w/v) BSA for 3 times, each for 5 min. Then, the membranes were incubated at room temperature together with 1×TBST containing secondary antibody (anti-rabbit-HRP or anti-rabbit-AP antibody, 1:5000 dilution) and 5% (w/v) BSA for 2 hours, then washed with 1×TBST containing 5% (w/v) BSA for 3 times, each for 5 min, followed by color development and photograph. As shown in FIGS. 2A and 2B, semi-quantitative calculation for protein expression level of subtype 1 and subtype M of STING was performed according to the stripes of targeting proteins.

Figures 3A, 3B:
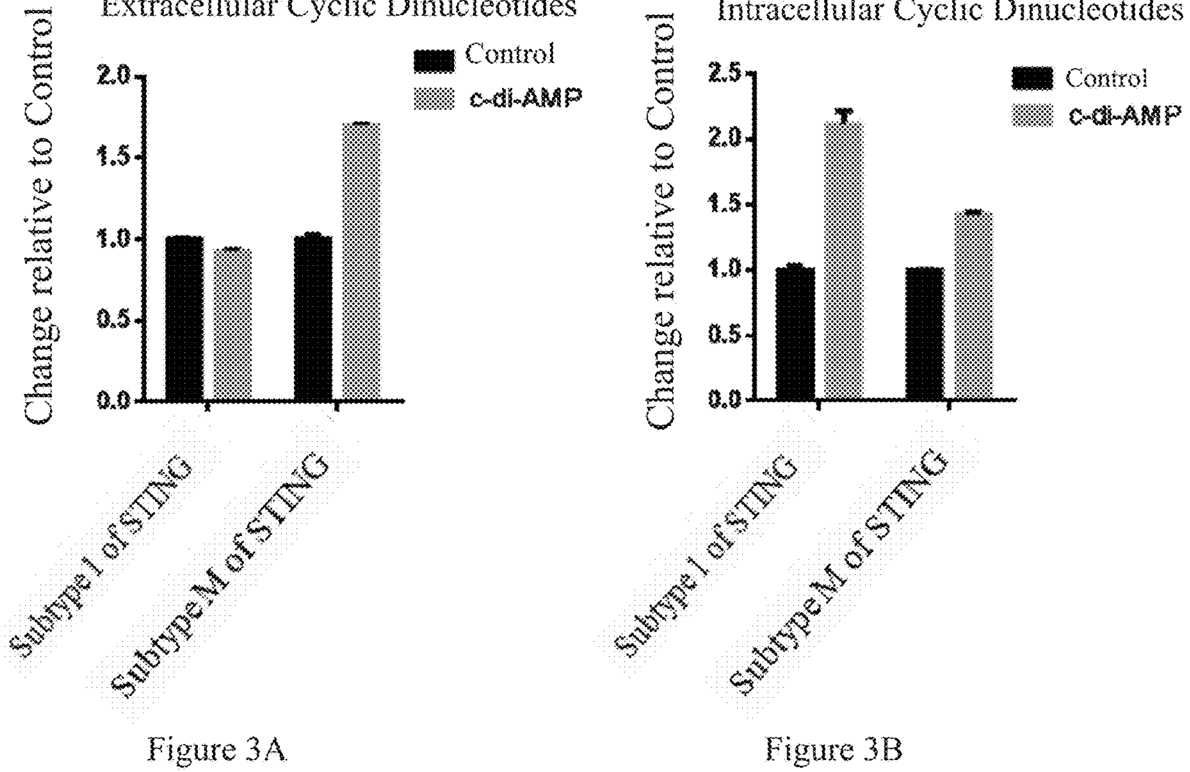
FIGS. 3A and 3B show that it can be seen that the subtype M of STING is the receptor that senses extracellular cyclic dinucleotides and activates generation of type 1 interferon by transfecting reporter plasmid of type 1 interferon into the cell lines for stably expressing subtype 1 and subtype M of STING. Both the subtype 1 and subtype M of STING can sense intracellular cyclic dinucleotides and activate generation of type 1 interferon.

Example 4: Subtype M of Human and Subtype M of Mouse STINGs were the Receptors that Sense Extracellular Cyclic Dinucleotides and Activate Generation of Type 1 Interferon The cell lines for stably expressing each subtype of STING were constructed by transducing subtypes 1 and 3 of mouse STING and subtypes 1 and M of human STING into different cell lines lack of STING with lentivirus. Meanwhile, these cell lines stably expressed reporter luciferase mediated by the promoter of type 1 interferon. The content of type 1 interferon within the cells or supernatants could be directly detected after adding these cell lines to the medium or the medium with 30 M extracellular cyclic dinucleotides c-di-AMP or transfecting c-di-AMP into cells by using lipofectamine 2000 for 16 hours, or cells were lysed and mixed with the substrate of the luciferase. The fluorescence intensities were read out. The ratio of the fluorescence intensities from the same cells with or without c-di-AMP was used to reflect increase of the fluorescence intensities obtained after adding c-di-AMP. It was demonstrated that subtype M of mouse STING and subtype M of human STING were the receptors that sense extracellular cyclic dinucleotides, while subtypes 1 and M of mouse and subtypes 1 and M of human STINGs could sense intracellular c-di-AMP (FIGS. 3A and 3B).

Example 5: Use of Stable Cell Strains in Screening Agonists for Subtypes M of Human and Mouse STINGs Step 1. The reporter cell lines for stably expressing subtype M of STING and the reporter genes of type 1 interferon provided by the kit mentioned above were laid on a 96-well plate, to which the medicaments to be screened were added.

For the reporter cell lines attached on the wall (e.g., HEK293T cell lines), it needed to pretreat the said cell lines with trypsin/EDTA for 10 min at 37° C. and the trypsin was neutralized in RPMI1640 with 10% fetal bovine serum. For the suspended reporter cell lines (e.g., THP-1 cell lines), centrifugation can be directly performed. After performing centrifugation for 5 min at 500 g, the cells were re-suspended in DMEM complete culture medium containing 10% fetal bovine serum, 100 U/mL penicillin and 100 g/mL streptomycin at a cell density of $1\times10^5$/ml. The cells were laid on a 96-well plate (200 L/well) and incubated in 5% $CO_2$ incubator at 37° C. for use. After 16 hours, the supernatants were withdrawn and 200 μl DMEM complete culture medium containing medicaments to be screened was added, and meanwhile, a positive control group (30 M c-di-AMP, InvivoGen, Product vac-cda) and a negative control group (merely with the culture medium without any medicaments) were established.

Since the promoter of type 1 interferon was further activated upon activating subtype M of STING, fluorescein reporter genes were added to downstream of the promoter of type 1 interferon. The expression of the luciferase reporter genes will be increased by the agonists for subtype M of STING, and the expression of type 1 interferon was also activated. The expression level of the luciferase could be measured through directly measuring the content of type 1 interferon in cells or supernatants, or through adding the substrate of the luciferase and reading the fluorescence volume generated by the substrate, thereby reflecting the activation degree for the promoter of type 1 interferon by the medicaments.

Step 2. The expression of the reporter genes upon adding the medicaments to be screened was monitored in real-time by using photometer.

At 16 hour after adding the medicaments, the supernatants were removed. 100 μl cell lysate was added to each well, followed by vibrating for 20 min. 20 μl cell lysate was mixed with 80 μl substrate of the luciferase. The fluorescence intensity of the substrate of the luciferase was measured by using photometer.

Step 3. The compounds for increasing the expression of the luciferase could be accurately and effectively screened out by using such system and the screened medicaments were agonists for subtype M of STING.

Figure 4:
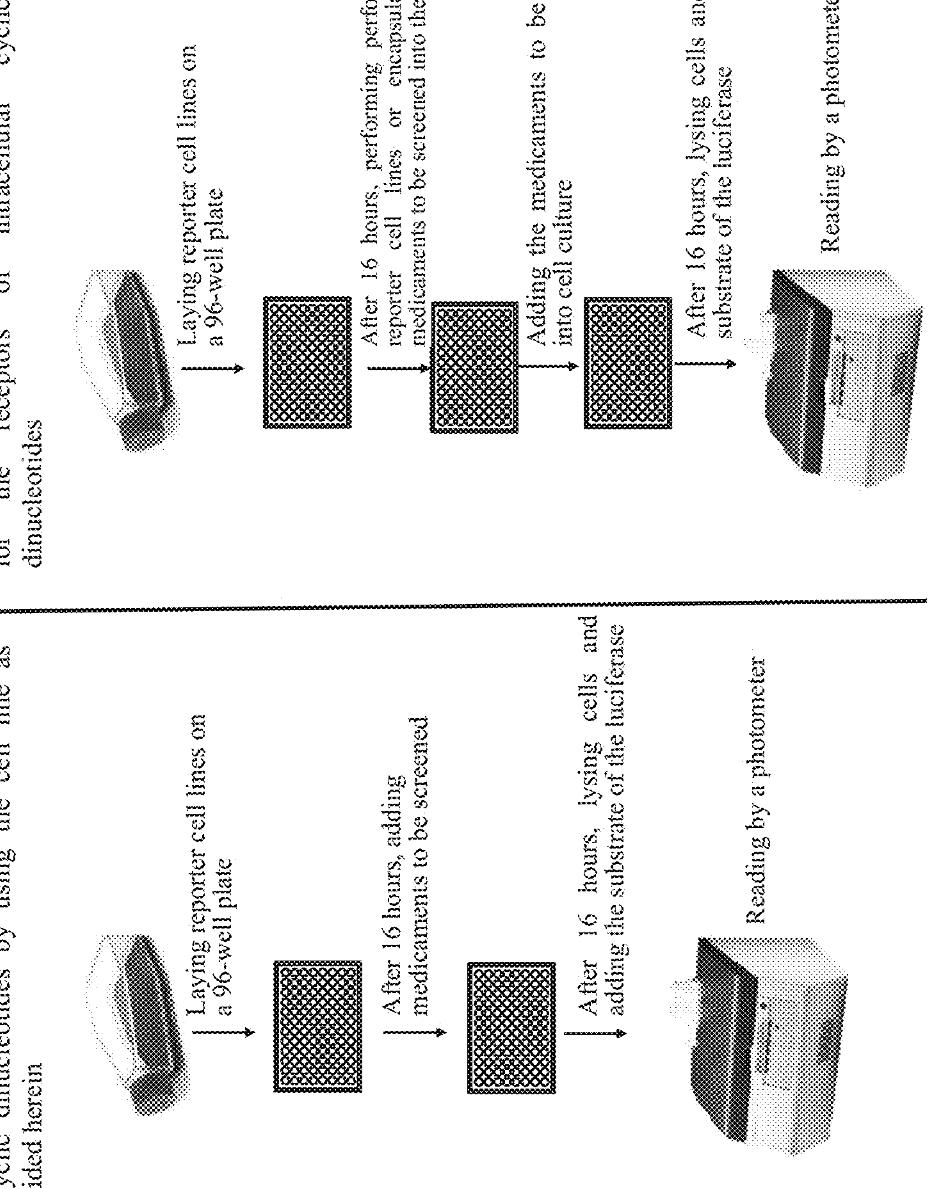
FIG. 4 shows the method for high-throughput screening medicaments according to the present disclosure and comparison of such method with the conventional method.

As shown in FIG. 4, as compared with the conventional method relating to the receptor STING of intracellular cyclic dinucleotides, in the method as provided herein, the step of perforation of the reporter cell lines or encapsulation of the medicaments into the liposome was omitted, thus the procedure for screening medicaments was simplified and the range of the medicaments that can be screened was expanded (for example, there is no need to encapsulate the medicaments into the liposomes).

Example 6: Use of the Stable Cell Lines in Screening the Inhibitors for Subtype M of STING Disclosed herein is a method for high-throughput screening the inhibitors for subtype M of STING based on the reporter cell lines established as described herein. The present invention is based on the fact that identification of exogenous ligands by subtype M of human and subtype M of mouse STING can be blocked by the extracellular anti-STING protein C terminal antibody (Abcam, Product ab189430).

Step 1. The stable cell lines of subtypes M of human and mouse STINGs provided by the kit mentioned above were laid on a 96-well plate.

For the reporter cell lines attached on the wall (e.g., HEK293T cell lines), it needed to pretreat the said cell lines with trypsin/EDTA for 10 min at 37° C. and the trypsin was neutralized in RPMI1640 with 10% fetal bovine serum. For the suspended reporter cell lines (e.g., THP-1 cell lines), centrifugation can be directly performed. After performing centrifugation for 5 min at 500 g, the cells were re-suspended in DMEM complete culture medium containing 10% fetal bovine serum, 100 U/mL penicillin and 100 g/mL streptomycin at a cell density of $1\times10^5$/ml. The cells were laid on a 96-well plate (200 L/well) and incubated in 5% $CO_2$ incubator at 37° C. for use.

After 16 hours, the supernatants were withdrawn and 100 μl DMEM complete culture medium containing medicaments to be screened was added, and meanwhile, a positive control group (50 g/ml anti-STING protein C terminal antibody (Abcam, Product ab189430)) and a negative control group (merely with the culture medium without any medicaments or antibodies) were established. After 2 hours, c-di-AMP (final concentration, 30 M, InvivoGen, Product vac-cda) was added.

Step 2. The expression of the reporter genes upon adding the medicaments to be screened was monitored in real-time by using photometer.

Since the promoter of type 1 interferon was further activated upon activating subtype M of STING, luciferase reporter genes were added to downstream of the promoter of type 1 interferon. The expression of the luciferase reporter genes will be increased due to the ligand c-di-AMP of subtype M of STING, and the expression of type 1 interferon was also increased. If the added medicaments could inhibit activation of the promoter of type 1 interferon and the expression of type 1 interferon per se, it could be indicated that the medicaments could inhibit the functions of subtypes M of human and mouse STINGs.

At 16 hour after adding c-di-AMP, the content of type 1 interferon in supernatants or the content of type 1 interferon within cells could be directly detected by ELISA, or the supernatants were removed. 100 μl cell lysate was added to each well, followed by vibrating for 20 min. 20 μl cell lysate was mixed with 80 μl substrate of the luciferase. The fluorescence intensity of the substrate of the luciferase was measured by using photometer.

Step 3. The compounds for inhibiting the expression of the luciferase could be accurately and effectively screened out by using such system and the screened medicaments were inhibitors for subtype M of STING.

As shown in FIG. 4, as compared with the conventional method relating to the receptor STING of intracellular cyclic dinucleotides, in the method as provided herein, the step of perforation of the reporter cell lines or encapsulation of the medicaments into the liposome was omitted, thus the procedure for screening medicaments was simplified and the range of the medicaments that can be screened was expanded (for example, there is no need to encapsulate the medicaments into the liposomes).

The foregoing is provided for illustration, and does not intend to limit the present disclosure. Any changes and modifications for the above embodiments come within the scope of the present disclosure.

The invention claimed is:

1. A method for screening agonists or inhibitors for receptors of extracellular cyclic dinucleotides, comprising the following steps:

culturing cells comprising a nucleotide sequence set forth in SEQ ID NO: 1 or SEQ ID NO: 2;

adding medicaments to be screened to a culture medium in which the cells are cultured, incubating the cells, detecting the content of type 1 interferon or NF KappaB within the cells or cell culture medium, or monitoring a reporter fluorescein produced by the cells to which the medicaments are added by a photometer; and screening out the medicaments for increasing or inhibiting the expression of type 1 interferon or a reporter gene.

2. The method of claim 1, wherein the medicaments to be screened are selected from the group consisting of synthetic chemical compounds, natural compounds, and biological medicaments.

3. A cell line, comprising a subtype M gene of human STING or a subtype M gene of mouse STING, wherein:

the subtype M gene of human STING is the nucleotide sequence set forth in SEQ ID NO:2, or is a nucleotide sequence encoding the amino acid sequence set forth in SEQ ID NO:4, and the subtype M gene of mouse STING is the nucleotide sequence set forth in SEQ ID NO:1, or is a nucleotide sequence encoding the amino acid sequence set forth in SEQ ID NO:3.

4. The cell line of claim 3, further comprising a reporter gene for indicating that the subtype M gene of human STING or the subtype M gene of mouse STING is activated.

5. The cell line of claim 4, wherein the reporter gene is located downstream of type 1 interferon or NK KappaB reaction element promoter.

6. The cell line of claim 3, further comprising:

a recombinant expression vector comprising the sequence set forth in SEQ ID NO:1 or SEQ ID NO:2; or a recombinant expression vector comprising the the nucleotide sequence encoding the amino acid sequence set forth in SEQ ID NO:3 or SEQ ID NO:4.

* * * * *